US011968981B2

(12) United States Patent
Gajendiran et al.

(10) Patent No.: US 11,968,981 B2
(45) Date of Patent: Apr. 30, 2024

(54) ANTI-VIRAL FORMULATION OF ACTIVE NANO INGREDIENTS FOR COATING ON PERSONAL PROTECTIVE EQUIPMENT AND FOR AEROSOL BASED DISINFECTANT COMPOSITION

(71) Applicant: Indian Oil Corporation Limited, Mumbai (IN)

(72) Inventors: Mani Gajendiran, Faridabad (IN); Ruchi Jain, Faridabad (IN); Arjyabaran Sinha, Faridabad (IN); Koushik Bhowmik, Faridabad (IN); Om Parkash, Faridabad (IN); Mukesh Kumar Vyas, Faridabad (IN); Jyotiranjan Ota, Faridabad (IN); Samik Kumar Hait, Faridabad (IN); Vivekanand Kagdiyal, Faridabad (IN); Deepak Saxena, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 134 days.

(21) Appl. No.: 17/211,068

(22) Filed: Mar. 24, 2021

(65) Prior Publication Data
US 2022/0110328 A1    Apr. 14, 2022

(30) Foreign Application Priority Data

Oct. 14, 2020    (IN) .............................. 202021044755

(51) Int. Cl.
| | |
|---|---|
| *A01N 59/20* | (2006.01) |
| *A01N 25/06* | (2006.01) |
| *A01N 59/14* | (2006.01) |
| *B82Y 5/00* | (2011.01) |
| *B82Y 30/00* | (2011.01) |
| *B82Y 40/00* | (2011.01) |

(52) U.S. Cl.
CPC .............. *A01N 59/20* (2013.01); *A01N 25/06* (2013.01); *A01N 59/14* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

2013/0091611 A1    4/2013  Oxford et al.
2020/0318283 A1    10/2020 Uddin et al.

FOREIGN PATENT DOCUMENTS

CN    102144817 B    9/2013
WO    2006/062826 A2    6/2006

OTHER PUBLICATIONS

Zhou et al., Advanced Fiber Materials (2020) 2:123-139 (Year: 2020).*
Mahmood et al., AAPS PharmSciTech (2020) 21:285. (Year: 2020).*
Aleksandra Loczechin et al., Functional Carbon Quantum Dots as Medical Countermeasures to Human Coronavirus, Oct. 21, 2019, ACS Appl. Mater. Interfaces 2019, 42964-42974, 11.
Pradip Dey et al., Multivalent Flexible Nanogels Exhibit Broad Spectrum Antiviral Activity by Blocking Virus Entry, Jun. 12, 2018, ACS NANO 2018, 6429-6442, 12.
Mori Y. et al: "Antiviral activity of silver nanoparticle/chitosan composites against H1N1 influenza A virus", Nanoscale Research Letters, vol. 8, No. 1, Feb. 1, 2013 (Feb. 1, 2013), pp. 1-6.
Agnihotri Shekhar et al: "Antimicrobial chitosan-PVA hydrogel as a nanoreactor and immobilizing matrix for silver nanoparticles", Applied Nanoscience, vol. 2, No. 3, Sep. 1, 2012 (Sep. 1, 2012), pp. 179-188.
Jelinkova Pavlina et al: "Nanoparticle-drug conjugates treating bacterial infections", Journal of Controlled Release, Elsevier, Amsterdam, NL, vol. 307, Jun. 19, 2019 (Jun. 19, 2019), pp. 166-185.
Hiragond Chaitanya B et al: "Enhanced anti-microbial response of commercial face mask using colloidal silver nanoparticles", Vacuum, Pergamon Press, GB, vol. 156, Aug. 16, 2018 (Aug. 16, 2018), pp. 475-482.
Rai Mahendra et al: "Broad-spectrum bioactivities of silver nanoparticles: the emerging trends and future prospects", Applied Microbiology and Biotechnology, Springer Berlin Heidelberg, Berlin/Heidelberg, vol. 98, No. 5, Jan. 10, 2014 (Jan. 10, 2014), pp. 1951-1961.
Jones, M. V., et al. "The use of bacteriophage MS2 as a model system to evaluate virucidal hand disinfectants." Journal of Hospital Infection vol. 17.4 (Jan. 14, 1991 ): pp. 279-285.

* cited by examiner

*Primary Examiner* — Jennifer Chin
(74) *Attorney, Agent, or Firm* — Workman Nydegger

(57) ABSTRACT

The present invention relates to an anti-viral nanoformulation suitable for diverse surface application in form of hydrogel based nanoemulsion, or an aerosol spray. The present invention discloses incorporation of nanomaterials such as functionalized carbon quantum dots (F-CQDs), copper nanoparticles (CuNPs) or silver nanoparticles (Ag-NPs) into the hydrogel (HG) scaffold to act as chemical barrier and anti-viral agent against SARS-CoV-2 or *Escherichia coli*: phage MS2. The nanoformulation is coated on personal protective equipment's (PPE) and different surfaces such as glass, steel and plastic to control viral infection including corona virus infection.

12 Claims, 8 Drawing Sheets

ANTI-VIRAL FORMULATION OF ACTIVE NANO INGREDIENTS FOR COATING ON PERSONAL PROTECTIVE EQUIPMENT AND FOR AEROSOL BASED DISINFECTANT COMPOSITION

FIELD OF THE INVENTION

The present invention relates to an anti-viral nanoformulation. In particular the invention relates to an anti-viral nanoformulation suitable for diverse surface application in form of nanohydrogel based emulsion or an aerosol spray.

BACKGROUND OF THE INVENTION

Corona viral infection is vigorously caused by inhalation of virus particles present in droplets of moisture. The virus particles with smaller size (<200 nm) could easily find their way into the human respiratory tract. The SARS or corona virus are spread by droplets produced by coughing or sneezing with sizes around 100-500 nm. Since, the pore size among fibers of facial mask is on average 10 to 30 μm, the corona virus could easily transmit through the existing common face masks. The global concern about airborne infective & highly contagious viruses such as corona virus (Covid-19), SARS, and swine flu (H1N1) viral infections is increased many-fold in the current scenario. However, solutions in terms of vaccine or medication to prevent or reduce the spread of the airborne viral infections are yet to be developed. The coating of nanomaterials on PPE is a promising way of reducing the infection of airborne viruses. For example, Ren et al have disclosed anti-viral formulations nanomaterials for use in reducing or preventing Avian H5N1 Influenza NIBRG-14b virus transmission (Ren et al. US 2013/0091611A1). They have coated silicon nitride, tungsten carbide, titanium carbide or titanium carbonitride on fibers of protective face mask and, found that the tungsten carbide nanoparticles inhibited the H5N1 virus like the positive control citric acid as anti-viral agent. In another example, the AgNPs and carbyne have been disclosed to exhibit anti-viral property (Jose eta al. WO2006/062826 A2). However, AgNPs could not alone control 100% of viral infection, and hence, further transmission of infection is possible.

Recently, the functionalized carbon quantum dots (F-CQDs) have been exploited as efficient agent for blocking and inhibiting human corona virus. Loczechin et al. have reported CQDS functionalized with amine and boronic acid functional groups inhibited the human corona virus HCoV-229E infection (Loczechin et al. ACS Appl. Mater. Interfaces 2019, 11, 42964-42974). The F-CQDs with amine and boronic acid functional groups without triazole ring exhibited excellent inhibitory activity on HCoV-229E, while the F-CQDs functionalized with triazole ring did not exhibit the inhibitory activity against HCoV-229E. However, the starting material used to synthesize the boronic acid functionalized CQDs is very expensive. Hence, an alternative synthetic methodology is being developed to synthesize F-CQDs to make use of the product to public at a comparatively lower cost. Recently, flexible hydrogel matrix has been reported to exhibit potential anti-viral activity. For example, Dey et al. have reported polyglycerol-based sulfated multivalent nanogels to inhibit Herpes simplex virus type 1 (HSV-1) infection (Dey et al. ACS Nano 2018, 12, 6429-6442). The flexible nanogels inhibited the viral infection more efficiently compared to a rigid hydrogel. The negative charge of sulfate group in the hydrogel could help to adhere the virus particles and inhibiting the viral infection.

OBJECTIVES OF THE PRESENT INVENTION

It is a primary objective of the invention to provide a multifunctional anti-viral nano formulation with F-CQDs and hybrid with metal or metal oxide nanoparticles in a nano-hydrogel scaffold.

It is the further objective of the present invention to provide cost-effective method to develop a multifunctional anti-viral coating formulation consists of F-CQDs, metal or metal oxide nanoparticles and nano hydrogel scaffold.

It is the further objective of the present invention to provide a methodology to control swelling ability of nanohydrogel and alteration of pore size to fabricate effective respirable and efficient PPEs to block viral spread and replication.

It is the further objective of the present invention to formulate a disinfectant spray based on the nanoformulation for application in diversified surfaces.

SUMMARY OF THE PRESENT INVENTION

Accordingly, the present invention provides an anti-viral nanoformulation for coating on personal protective equipment and as an aerosol based disinfectant composition and a method of preparation of the same.

In one feature of the present invention provides a multifunctional anti-viral formulation comprising of:
  a. functionalized-Carbon Quantum Dots (F-CQDs) in range of 20-500 ppm of the total volume;
  b. metal or metal oxide nanoparticles in range of 20-500 ppm of the total volume; and
  c. nano hydrogel in range of 50-1000 ppm of the total volume.
  wherein the formulation is a nanoemulsion or aerosol spray.

In another feature of the present invention, functional carbon quantum dots are boron or nitrogen doped.

In one feature, the present invention, metal, or metal oxide nanoparticles are selected from Cu, CuO, and Ag.

In another feature of the present invention, nano hydrogel fabricated using cross-linkable synthetic polymer and natural polymer acts as a scaffold for the anti-viral active nanomaterials.

In another preferred feature of present invention, the nanodispersion combination has shown 99% anti-viral efficacy against SARS Cov-2.

In one feature of the present invention, anti-viral formulation is coated on porous surfaces and/or non-porous surfaces.

In another preferred feature of the present invention, anti-viral formulation is coated on personal protective equipment's, face masks, face shields, or cotton clothes.

In another preferred feature of the present invention, formulation is suspended in aerosol selected from the group ethanol/methanol/isopropanol/butane/LPG or a mixture thereof to prepare a disinfectant spray.

In another preferred feature of the present invention, process of preparation of anti-viral formulation in steps of:
a. nanomaterials i.e., hydrogel, F-CQDs, AgNPs or CuNPs are mixed in double distilled water (DDW);
b. 20-50 µL of each tetramethyl ethylenediamine (TE-MED) and aqueous ammonium persulphate (5-15% w/v) added to (a);
c. emulsifier (0.2-2% w/v) dissolved in organic solvent;
d. mixtures of step (b) and (c) ultrasonicated for 5-15 minutes.
e. Emulsifier selected form Sorbitan monolaurate, Sorbitan monostearate, Sorbitan monopalmitate.
f. wherein organic solvent selected from n-hexane, n-heptane, dichloromethane (DCM).

In another preferred feature of the present invention, aerosol based disinfectant spray with anti-viral formulation as active ingredient has been prepared and their durability on different surfaces has been studied.

Various objects, features, aspects, and advantages of the present invention will become more apparent from the following detailed description of preferred embodiments of the invention.

BRIEF DESCRIPTION OF DRAWINGS

FIG. 5(b) is an optical microscope image of nanoformulation in a higher magnification.

DESCRIPTION OF THE INVENTION

Figure 1:
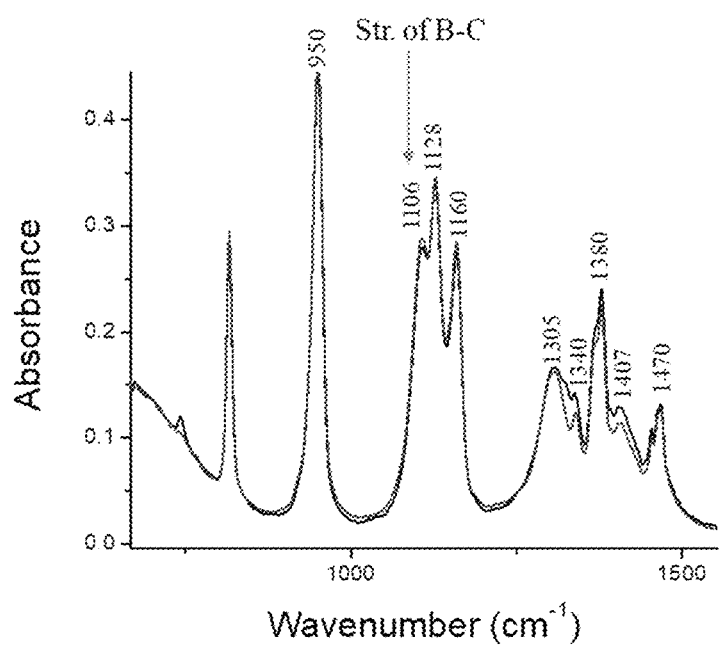
FIG. 1: Characterization of F-CQDs by FTIR technique.

The present invention provides an antiviral coating formulation suitable for diverse surface application in form of nanohydrogel based emulsion or an aerosol spray. In particular, the anti-viral nanoformulation comprises active nano ingredients and is useful in coating of personal protective equipments and disinfecting different surfaces such as plastic, glass and steel etc. The same nanodispersion also can be incorporated in aerosol based disinfectant spray having similar anti-viral activity, where the aerosol is based on ethanol/methanol/isopropanol/butane/LPG or a mixture thereof.

In one embodiment, the present invention deals with synthesis of polymers and fabrication of hybrid HG. The HG scaffold used here is fabricated using a synthetic polymer and a modified natural polymer.

In a preferred embodiment, the nanomaterials such as F-CQDs (50-500 ppm), AgNPs (20-200 ppm) and CuNPs (50-500 ppm) loaded hybrid nanoHG (50-1000 ppm) emulsion is described to be effective in limiting the growth of viruses such as SARS-Covid-2 and *Escherichia coli*: phage MS2.

In another preferred embodiment, the present invention describes various nanomaterial compositions used as anti-viral agents. The nanomaterial compositions used but not limited to are F-CQDs (preferable size range: 2-20 nm), AgNPs (preferable size range: 5-50 nm) and CuNPs (preferable size range: 2-30 nm).

In yet another preferred embodiment, the present invention describes the preparation of HG scaffold using cross-linkable synthetic polyester and a natural polymer via thermal cross-linking. The synthetic polyester used but not limited to are polycaprolactone (PCL-PEG), poly (lactic-co-glycolic acid-PEG) PLGA-PEG, and poly tricarboxylic or dicarboxylic acid-b-PEG). The natural polymer used but not limited to are chitosan, gelatin, and collagen.

In one of the preferred embodiments, the present invention describes preparation of nanoHG formulation with incorporated nanoparticles in w/o emulsification technique. The used organic solvents but not limited to are dichloromethane (DCM), n-hexane, and n-heptane. The emulsifier used is Span20 with variable concentration in organic phase.

In accordance with another major embodiment, the present invention describes the anti-viral efficacy of the individual nanoparticles in HG as well as composite of the nanoparticles in presence of HG. In all the examples the viral efficacy of log reduction of more than 99% is achieved within 15 seconds, more than 99.5% is achieved within 30 seconds, and more preferably 99.99% is achieved within 60 seconds.

In accordance with another major embodiment, the invention describes the anti-viral efficacy of the individual nanoparticles in HG as well as composite of the nanoparticles in presence of HG against SARS COV-2. An efficacy of 99% was achieved for different combination of nanoparticles.

In accordance with another embodiment, the present invention describes about the development of nanoparticle incorporated antiviral nanoHG formulation coated PPE porous surfaces such as face mask laboratory coats and non-porous surfaces such as steel, plastic, wood, glass etc.

In accordance with another preferred embodiment, this invention deals with coating of nanoemulsion on PPE such as face mask, face shields or cotton clothes. The nanomaterials loaded HG nano-emulsion was sprayed on cotton clothes and mask. The nano-HG acts as a scaffold for nanomaterials as well as an anti-viral agent. The boron doped F-CQDs could assemble on surface of viral particles, and inhibit the viral entry in to the target cell. The AgNPs and CuNPs could exhibit a chemical barrier and effectively deactivate the viral particles.

The nano-hydrogel with muco-adhesive property could effectively absorb the corona virus containing droplets and the corona virus could be trapped in the scaffold. The F-CQDs, Cu or CuO NPs or Ag NPs inhibit the corona virus by chemically attaching themselves. In addition, the carboxylic acid enriched hydrogel scaffold would provide an acid environment to effectively inhibit the spread of corona virus. Combination of active ingredients is also to act as effective coating material to sanitize different surfaces and prohibit the transmission of viral spread.

In accordance with another major embodiment, aerosol based surface disinfectant spray was prepared with different combination of nanodispersion, using ethanol/isopropanol/butane/LPG as aerosol base. The disinfectant spray can be used to disinfect different surfaces such as steel, glass, plastic, wood, fabric etc. The active anti-viral ingredients found intact even after several touches and wipes on the surface.

Example 1: Synthesis of Cross-Linkable Polymers (CL-Pol)

The synthetic polymer used here but not limited to are PLGA-b-PEG, PCL-b-PEG and a poly tricarboxylic or dicarboxylic acid-b-PEG. The specified synthetic polymers were reacted with glycidyl methacrylate (2-40%) to obtain cross-linkable synthetic polymers. The natural polymers used here but not limited to are chitosan, gelatin and collagen. The natural polymers were modified with maleic acid (2-30%) to get cross-linkable natural polymers.

Example 2: Synthesis of B and N Doped Functional Carbon Quantum Dots (F-CODs)

Figure 2:
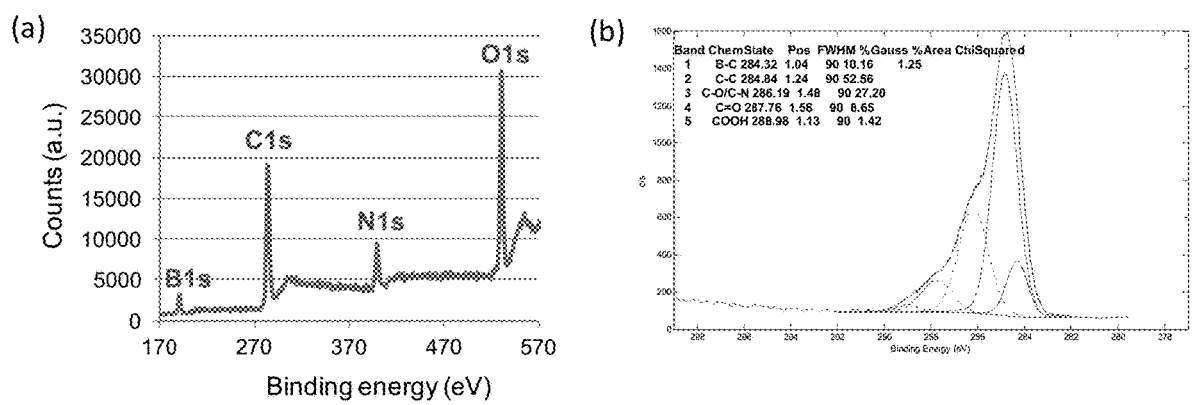
FIG. 2(a) is characterization of F-CQDs by X-Ray photo electron spectroscopy (XPS) survey spectrum.
FIG. 2(b) is a core level XPS spectrum of F-CQDs.

B and N doped CQDs were synthesized via solvo-thermal process. In brief, citric acid, boric acid and ethylenediamine (EDA) in ratio (1:1:1 w/w) were mixed in double distilled water and packed in a stainless steel autoclave. Then, the reaction mixture was hydrothermally treated at 150-200° C. for 3-8 h and cooled to room temperature. Reddish brown color solution of B and N doped F-CQDs were collected and stored at room temperature for further use. The F-CQDs were characterized by FTIR and X-Ray photo electron spectroscopy (XPS) (FIGS. 1 and 2).

Example 3: Synthesis of Silver Nanoparticles

Figure 3:
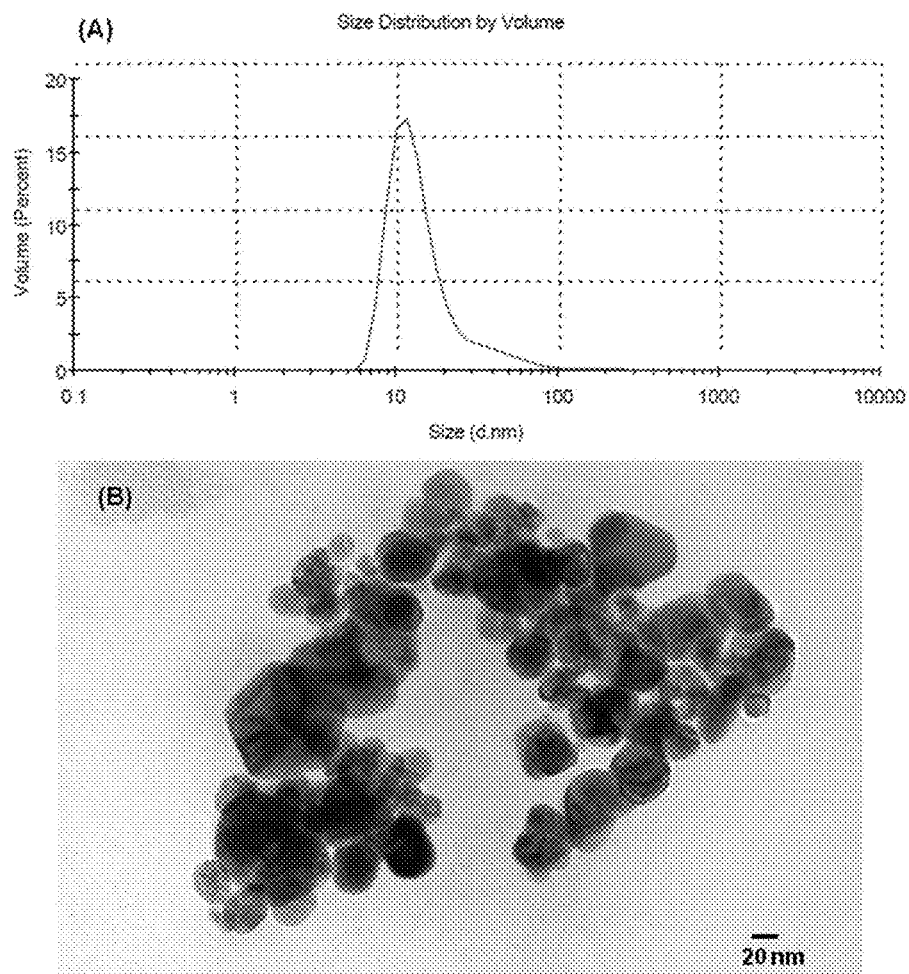
FIG. 3: Characterization of AgNPs by (A) DLS spectrum and (B) transmission electron microscopy (TEM) techniques.

In a typical procedure, polyvinylpyrrolidone (PVP, Molecular weight=10000-40000), was completely dissolved in DI water. This solution was stirred vigorously in a reactor fitted with a reflux condenser, followed by heating at 60-120° C. Subsequently, calculated amount of silver nitrate, used as a precursor of Ag, was dissolved in DI water, and added promptly into the reactor. The reaction was maintained for 30 min at the above mentioned reaction temperature. After the reaction was completed, the solution was cooled to room temperature, yellowish brown color indicates the formation of AgNPs. The Ag NPs were characterized by DLS spectrum and TEM image (FIG. 3).

Example 4: Synthesis of Copper Nanoparticles

Figure 4:
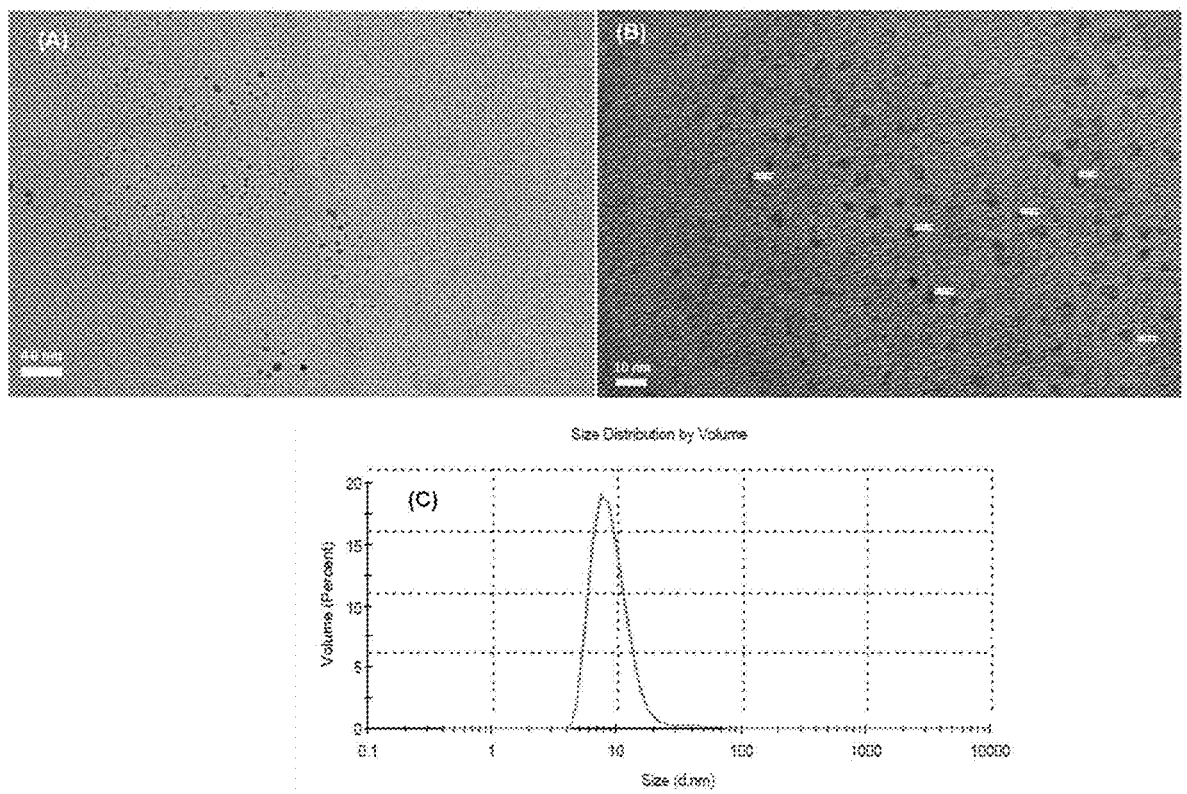
FIG. 4: Characterization of CuNPs by (A), (B) TEM and (C) DLS techniques.

In a typical procedure, aqueous solution of Cu precursor along with PVP was heated at 60° C. under atmospheric conditions. PVP was used as capping agent with copper to PVP ratio ~10:1. A solution of ascorbic acid was subsequently added under vigorous stirring. The initial blue color turned to dark green immediately. The stirring was continued for 12 h generating a dark brown solution. The reaction solution was cooled to room temperature (RT) and centrifuged to remove larger agglomerates, if any. The resulting supernatant dispersion of Cu nanoparticle was collected and used for further characterization. The CuNPs were characterized by transmission electron microscopy (TEM) technique (FIG. 4).

Example 5: Preparation of Nano-Materials Loaded Hydrogel Nanoformulation

The anti-viral nanoformulation was prepared with different combination of CL-Pol, F-CQDs, AgNPs or CuNPs. Briefly aqueous solutions of different amounts of CL-Pol, F-CQDs, AgNPs or CuNPs were mixed together to obtain anti-viral nanoformulations with a preferred concentration of CL-Pol (50-1000 ppm), F-CQDs (50-500 ppm), AgNPs (25-400 ppm) or CuNPs (50-500 ppm). The prepared nanoformulations were used for preparing nanoemulsion for coating on PPE or aerosol based disinfectant spray separately.

Figure 5:
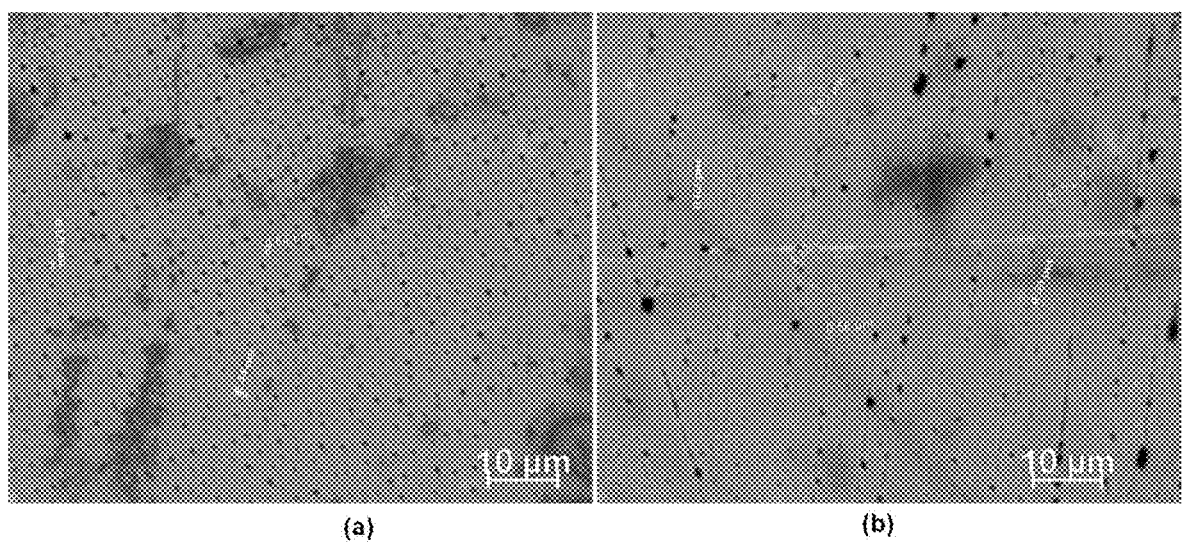
FIG. 5 (a) is characterization of nanoformulation by an optical microscope.
Figure 6:
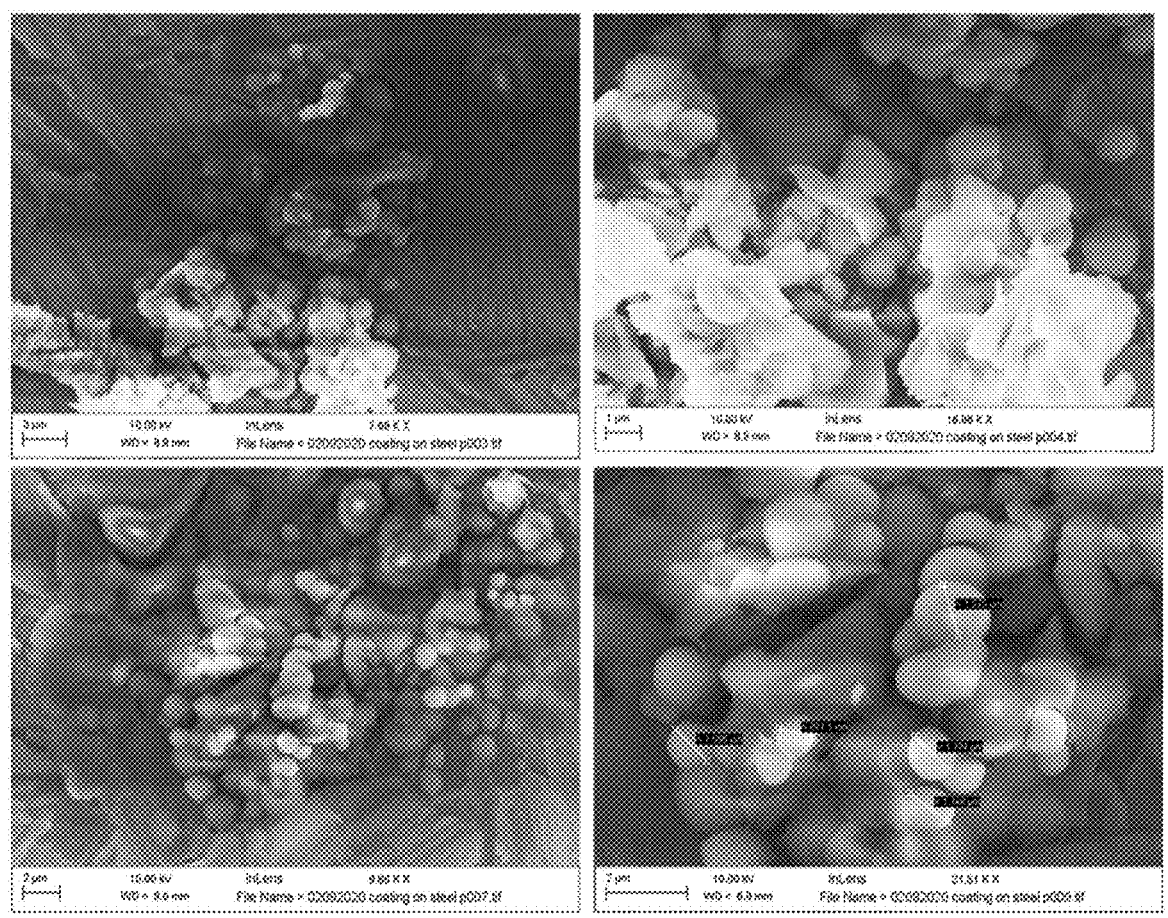
FIG. 6: Characterization of nanoformulation by SEM technique.

Example 6: Preparation of Anti-Viral Nanoemulsion and Spray Coating of Nano-Emulsion on Cotton Cloth The w/o emulsification technique was adopted to fabricate nano-materials loaded HG nano-emulsion. Briefly CL-Pol (50-500 ppm), F-CQDs (50-1000 ppm), AgNPs (25-400 ppm) or CuNPs (50-500 ppm) were mixed together in 2-30 mL of double distilled water (DDW) (Aqueous phase). Span20 as emulsifier (0.2-2% w/v) was dissolved in 70-98 mL of organic solvent (i.e. n-hexane or n-heptane or dichloromethane (DCM)) (Organic phase). Before adding the organic phase to aqueous phase, 20-50 µL of each tetramethyl ethylenediamine (TEMED) and aqueous ammonium persulphate (5-15% w/v) were added to aqueous phase. Then the organic phase was mixed with aqueous phase and ultrasonicated for 5-15 min to obtain nanomaterials loaded HG nanoformulations. In the nanoformulations, the concentration of CL-Pol varied from 50-1000 ppm, while concentration of F-CQDs or AgNPs or CuNPs varied from 20-500 ppm. The nanoformulations prepared for coating on cotton cloth were characterized by optical microscope and SEM techniques (FIGS. 5 and 6 respectively).

Figure 7:
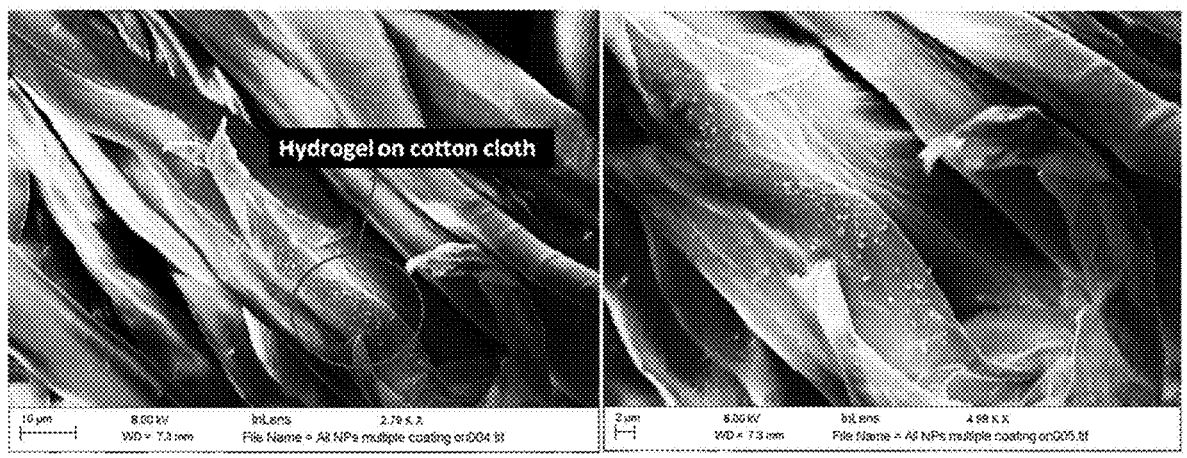
FIG. 7: Characterization of nanoformulation coated cotton cloths by SEM technique.
Figure 8:
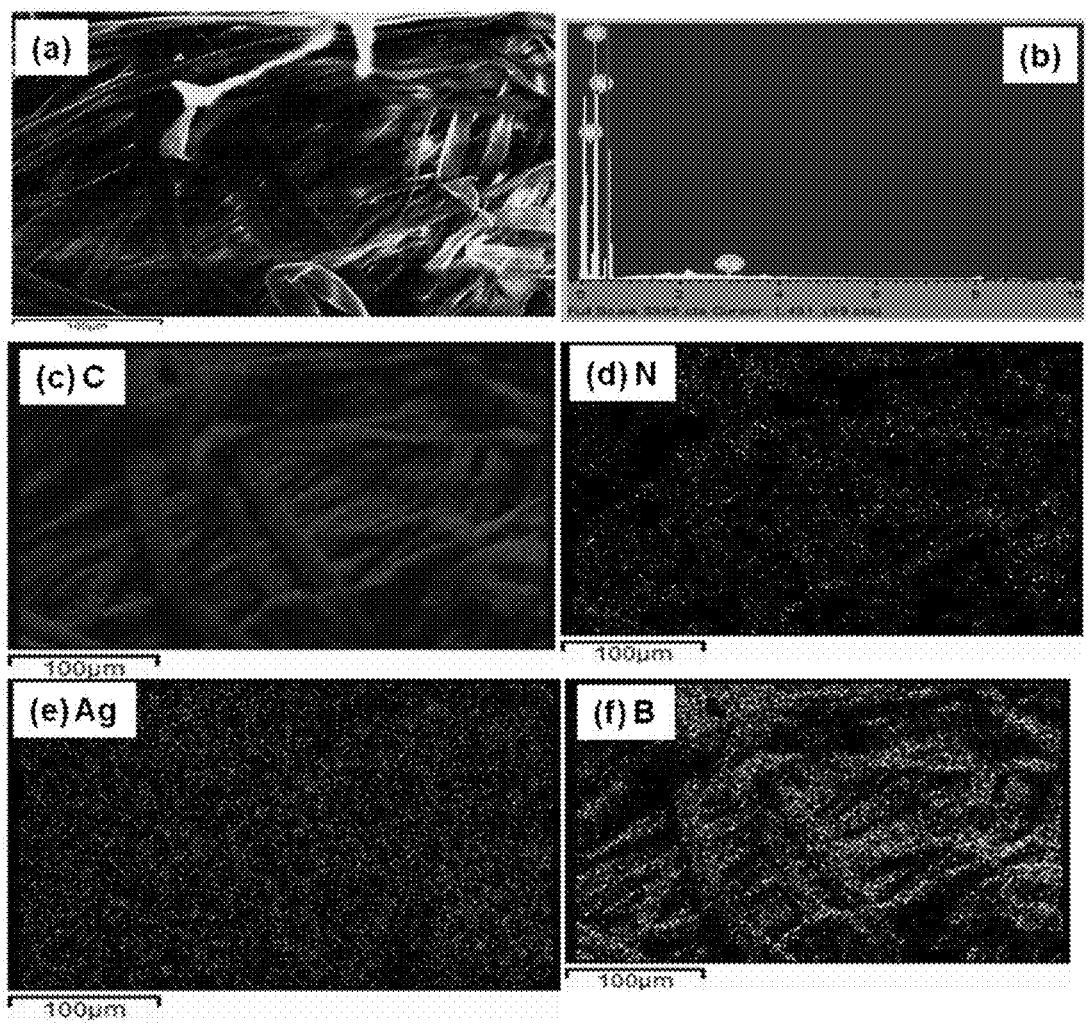
FIG. 8(a) is characterization of nanoformulation coated cotton cloth by scanning electron microscope (SEM)
FIG. 8(b) is energy dispersive spectrum (EDS) of nanoformulation from coated cotton cloth.
FIG. 8(c) is elemental mapping of carbon by Energy dispersive spectrum (EDS)
FIG. 8(d) is elemental mapping of nitrogen by Energy dispersive spectrum (EDS)
FIG. 8(e) is elemental mapping of silver by Energy dispersive spectrum (EDS)
FIG. 8(f) is elemental mapping of boron by Energy dispersive spectrum (EDS).

The nanomaterials loaded HG nanoemulsions were spray coated on cotton cloths. Briefly, 2-5 mL of sprayable HG nanoemulsions were spray coated on a cotton cloth with dimension 18"×4" (L W) and dried at room temperature (30-35° C.) for overnight. Multiple formulations such as (HG+AgNPs) or (HG+CQDs) or (HG+AgNPs+CQDs) or (HG+CuNPs) or (HG+CuNPs+CQDs) were prepared and coated on cotton cloth. The nanoformulation coated cotton cloths were characterized by SEM, EDS spectral and elemental mapping (FIGS. 7 and 8). The nanoformulation coated cotton cloth (3"×3" L×W) was immersed in phosphate buffer (pH7.4) and incubated for 24 h. Then the solution was analyzed by inductively coupled atomic emission spectroscopy (ICP-AES) to identify presence of coated nanomaterials by leaching out in the dissolution medium.

Example 7: Washing and Durability Studies of Nano-Formulation Coated Cotton Cloths The nanoformulation coated 50 cotton clothes were washed once per day using detergent solution for three weeks and dried under room temperature. 10 clothes were withdrawn from the experimental group every week and evaluated for remaining active component. Among those 10 masks, 5 masks were immersed in dil. $HNO_3$ (2-4 M) to extract the active elements from the cotton cloths, and 5 masks acted as control. The concentration of elements such as B and Cu present in the nitric acid extract was determined by ICP-MS technique and taken as reference for durability study. The percentage of active elements retained, and durability of the coated cotton cloths are represented in the Table 1. The data shows the presence of active components even after 3 weeks or ate last 21 washing.

TABLE 1

| | Percentage of active elements retained after washing (%) | |
|---|---|---|
| Time duration | B | Cu |
| Week 1 | 51.4 | 94.0 |
| Week 2 | 21.9 | 38.0 |
| Week 3 | 17.5 | 14.5 |

Example 8: Aerosol Based Spray of Nano-Formulations on Various Surfaces (Steel, Glass and Plastic) and their Durability Study Nanomaterials based spray-able aerosol prepared with butane as a propellant and active component in ethanol. The spray was applied on various selected surfaces like steel, glass and plastic (face shield) and durability of the spray in terms of presence of active components was studied by EDAX technique. The surfaces were subjected to several touches by hand and also by wipe. The surfaces again studied for presence of active component after fixed frequency. The durability of active components were investigated by the amount Ag taking as reference for a selected formulation. The elemental analysis data is provided in Table 2. All these data suggest presence of active component even after 25 touches.

TABLE 2

| Nano-formulation spray on | Element Weight % (Ag) | | |
|---|---|---|---|
| different surfaces | Steel surface | Glass surface | Plastic surface |
| Coated surface as such | 0.61 | 0.32 | 0.12 |
| 25 times touch | 0.46 | 0.09 | 0.02 |
| 50 times touch | 0.11 | 0.00 | 0.00 |
| 25 times wipe | 0.45 | 0.13 | 0.06 |
| 50 time wipe | 0.09 | 0.02 | 0.00 |

Example 9: Anti-Viral Activity of Nano-Formulations Against *Escherichia coli*: Phage MS2

The anti-viral activity of different formulations such as HG (or) HG+AgNPs (or) HG+CQDs (or) HG+AgNPs+CQDs) (or) the combination as described in Table 3 was tested on *Escherichia coli*: phage MS2 (ATCC 15597 B1) by following anti-viral protocol (Reference: Jones, M. V., et al. "The use of bacteriophage MS2 as a model system to evaluate virucidal hand disinfectants." Journal of Hospital Infection 17.4 (1991): 279-285). The anti-viral activity tests were performed at different time points (i.e., 15 or 30 or 60 sec) after incubation with nanoformulations. The anti-viral results are quantified by comparison with untreated control group and represented in Table 3.

TABLE 3

| | | Inactivation efficiency (%) at different contact time(in seconds) | | |
|---|---|---|---|---|
| S. No | Formulation | 15 Sec | 30 Sec | 60 Sec |
| 1 | HG (500 ppm) | 99.11% | 99.82% | 99.99% |
| 2 | HG (500 ppm) + Ag (100) | 99.22% | 99.84% | 99.99% |
| 3 | HG + CQD (200) | 99.35% | 99.88% | 99.99% |
| 4 | HG (500) + CQD (200) + Ag (100) | 99.64% | 99.98% | 99.99% |
| 5 | HG (500) + CQD (250) + Ag (250) | 98.94 | 99.45 | 99.88 |
| 6 | HG (500) + CQD (400) + Ag (400) | 99.13 | 99.84 | 99.96 |
| 7 | HG (500) + CQD (200) + Ag (100) | 98.08 | 99.04 | 99.58 |
| 8 | HG (500) + CQD (400) + Cu (400) | 98.91 | 99.47 | 99.75 |

Example 11: Anti-Viral Activity of Nanoformulations Against SARS-CoV-2

The anti-COVID19 activity of nanoformulations was tested on SARS-CoV-2 by following the standard method for accessing anti-viral activity (ASTM: E1052). Mag-MAX™ Viral/Pathogen Extraction Kit (Thermo Fisher) and Fosun COVID-19 RT-PCR Detection Kit (FOSUN PHARMA) were used to perform viral extraction assay and real-time reverse transcription-PCR (qRT-PCR) assay respectively. The different formulations and their ant-COVID results are represented in Table 4.

TABLE 4

| Sl. No. | Component (ppm) in aqueous solution | SARS-CoV-2 reduction (%) at different dilution after 5 minute incubation | | | | | |
|---|---|---|---|---|---|---|---|
| | | [a]5% | [a]10% | [a]25% | [a]50% | [a]70% | [b]100% |
| 1. | HG (500 ppm) | 25 | 35 | 23 | 38 | 51 | 40 |
| 2. | HG (500 ppm) + AgNPs (100 ppm) | 50 | 97 | 99 | 99 | 99 | 99 |
| 3. | HG (500 ppm) + F-CQDs (200 ppm) | 20 | 40 | 20 | 40 | 48 | 48 |
| 4. | HG (500 ppm) + CuNPs (400) | 85 | 78 | 89 | 99 | 99 | 99 |
| 5. | HG (500 ppm) + F-CQDs (200) + AgNPs (100) | 15 | 30 | 20 | 35 | 48 | 40 |
| 6 | HG (500 ppm) + F-CQDs (200 ppm) + CuNPs (400 ppm) | 85 | 70 | 99 | 93 | 99 | 99 |

[a]Components at different dilutions,
[b]Components without dilution.

Advantages of the Present Invention

Synthetic/natural polymer hybrid nano-hydrogel as a scaffold matrix for population of anti-viral nano-materials Use of nano-materials such as F-CQDs, Cu or CuO NPs, Ag NPs and related metallic nano-materials as chemical barrier to act as anti-viral agents Coating formulation on fabrics and PPE such as face masks, face shields, laboratory jackets etc. made out of those Nano-size of hydrogel ensures not to block the air flow in the mask, in addition it to inhibiting the corona virus to respiratory organ to maximum extent Nano-coating on the PPE act as a shield to inhibit the viral entry to respiratory tract Nano-hydrogel platform has versatility to incorporate multiple functional nano-materials and other anti-viral drugs alone or in combination Lower cost, and provides easiest method to develop anti-corona virus PPE Combination of active ingredients to act as effective coating material to sanitize different surfaces and prohibit the transmission of viral spread.

We claim:

1. An antiviral nano-formulation comprising:
   a. functionalized-Carbon Quantum Dots (F-CQDs) in a range of 20-500 ppm of a total volume of the nano-formulation;
   b. metal or metal oxide nanoparticles in a range of 20-500 ppm of the total volume of the nano-formulation; and
   c. a cross-linkable polymer (CL-Pol) in a range of 50-1000 ppm of the total volume of the nano-formulation, wherein the nano-formulation is a nano-emulsion or an aerosol spray,
wherein the cross-linkable polymer is a synthetic polymer or a natural polymer, and wherein the synthetic polymer is selected from the group consisting of polycaprolactone (PCL-PEG), poly (lactic-co-glycolic acid-PEG) (PLGA-PEG), and poly tricarboxylic or dicarboxylic acid-b-PEG, and the natural polymer is selected from the group consisting of chitosan, gelatin, collagen, and a combination thereof.

2. The nano-formulation as claimed in claim 1, wherein the metal or metal oxide nanoparticles are selected from the group consisting of AgNPs, CuNPs, CuONPs, and a combination thereof.

3. The nano-formulation as claimed in claim 2, wherein the AgNPs and CuNPs have a particle size of 5-50 nm and 2-30 nm respectively.

4. The nano-formulation as claimed in claim 2, wherein the nano-formulation comprises 200 ppm of F-CQDs, 500 ppm of the cross-linkable polymer, and 400 ppm of the CuNPs of the total volume of the nano-formulation.

5. The nano-formulation as claimed in claim 1, wherein the F-CQDs are Boron or Nitrogen doped.

6. The nano-formulation as claimed in claim 1, wherein the F-CQDs have a particle size of 2 to 20 nm.

7. The nano-formulation as claimed in claim 1, wherein the nano-formulation is suspended in an aerosol to form the aerosol spray, wherein the aerosol is selected from the group consisting of ethanol, methanol, isopropanol, butanol, liquified petroleum gas (LPG), and a mixture thereof.

8. The antiviral nano-formulation as claimed in claim 1, is capable of inactivating 99% of *Escherichia coli*: phage MS2 within 60 seconds.

9. The antiviral nano-formulation as claimed in claim 1, is capable of inhibiting 99% of SARS-CoV-2 within 5 minutes of incubation time.

10. A process for preparation of a nano-formulation for an antiviral coating emulsion, the process comprising steps of:
   a. mixing a cross-linkable polymer, F-CQDs, and metal or metal oxide nanoparticles in double distilled water (DDW) to form an aqueous solution, wherein the metal or metal oxide nanoparticles are selected from the group consisting of AgNPs, CuNPs, CuONPs, and a combination thereof;
   b. adding 20-50 μL of tetramethyl ethylenediamine (TE-MED) and 20-50 μL of aqueous ammonium persulphate (5-15% w/v) to the aqueous solution of step (a);
   c. dissolving an emulsifier (0.2-2% w/v) in an organic solvent;
   d. mixing solutions of step (b) and (c) and ultrasonicating for 5-15 minutes to obtain a nanomaterial loaded hydrogel nano-formulation,
   wherein the emulsifier is selected from the group consisting of Sorbitan monolaurate, Sorbitan monostearate, and Sorbitan monopalmitate, and wherein the organic solvent is selected from the group consisting of n-hexane, n-heptane, and dichloromethane (DCM).

11. The process as claimed in claim 10, further comprising synthesising the cross linkable polymer by crosslinking a synthetic polymer with 2-40% glycidyl methacrylate, wherein the synthetic polymer is selected from the group consisting of polycaprolactone (PCL-PEG), poly (lactic-co-glycolic acid-PEG) (PLGA-PEG), and poly tricarboxylic or dicarboxylic acid-b-PEG.

12. The process as claimed in claim 10, further comprising synthesising the cross-linkable polymer by crosslinking a natural polymer with 2-30% maleic acid, wherein the natural polymer is selected from the group consisting of chitosan, gelatin, collagen, and a combination thereof.

* * * * *